United States Patent
Griffin

(10) Patent No.: US 10,278,852 B2
(45) Date of Patent: May 7, 2019

(54) STEERABLE CATHETER WITH MULTIPLE BENDING RADII VIA A STEERING MECHANISM WITH TELESCOPING TUBULAR COMPONENTS

(71) Applicant: Medtronic Vascular, Inc., Santa Rosa, CA (US)

(72) Inventor: Patrick Griffin, Ballybrit (IE)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 443 days.

(21) Appl. No.: 15/065,938

(22) Filed: Mar. 10, 2016

(65) Prior Publication Data

US 2017/0258614 A1    Sep. 14, 2017

(51) Int. Cl.
*A61F 2/966* (2013.01)
*A61M 25/01* (2006.01)

(52) U.S. Cl.
CPC ......... *A61F 2/966* (2013.01); *A61M 25/0147* (2013.01); *A61M 25/0136* (2013.01); *A61M 2025/015* (2013.01); *A61M 2025/0175* (2013.01)

(58) Field of Classification Search
CPC .......... A61M 25/0136; A61M 25/0147; A61M 2025/015; A61M 2025/0175
See application file for complete search history.

(56) References Cited

U.S. PATENT DOCUMENTS

| | | |
|---|---|---|
| 5,318,525 A | 6/1994 | West et al. |
| 5,342,300 A | 8/1994 | Stefanadis et al. |
| 5,876,373 A | 3/1999 | Giba et al. |
| 6,132,390 A | 10/2000 | Cookston et al. |
| 7,717,875 B2 | 5/2010 | Knudson et al. |
| 7,780,723 B2 | 8/2010 | Taylor |
| 8,118,866 B2 | 2/2012 | Herrmann et al. |
| 2003/0050598 A1 | 3/2003 | Hayzelden |
| 2007/0005131 A1 | 1/2007 | Taylor |
| 2008/0065011 A1 | 3/2008 | Marchand et al. |
| 2011/0245917 A1 | 10/2011 | Savage et al. |

(Continued)

FOREIGN PATENT DOCUMENTS

| | | |
|---|---|---|
| GB | 2433700 | 12/2007 |
| WO | WO2012/019232 | 2/2012 |

OTHER PUBLICATIONS

PCT/US2017/020974, The International Search Report and the Written Opinion of the International Searching Authority, dated Jun. 1, 2017.

*Primary Examiner* — Ashley L Fishback
(74) *Attorney, Agent, or Firm* — Medler Ferro Woodhouse & Mills PLLC

(57) ABSTRACT

A steerable catheter includes a tubular sheath having a longitudinally-extending lumen formed within a wall thereof and a steering mechanism disposed within the longitudinally-extending lumen. The steering mechanism includes a pull tube and a pull wire. At least a segment of the pull wire is coaxially disposed within the pull tube. The pull tube has a distal end attached at a first anchor point to the tubular sheath, and the pull wire has a distal end attached at a second anchor point to the tubular sheath. The second anchor point is distal of the first anchor point. The pull tube and the pull wire are separately tensioned to bend respective regions of the tubular sheath.

20 Claims, 8 Drawing Sheets

(56) References Cited

U.S. PATENT DOCUMENTS

| | | |
|---|---|---|
| 2011/0251675 A1 | 10/2011 | Dwork |
| 2011/0251681 A1 | 10/2011 | Shipley et al. |
| 2011/0251682 A1 | 10/2011 | Murray, III et al. |
| 2011/0264202 A1 | 10/2011 | Murray, III et al. |
| 2012/0277671 A1* | 11/2012 | Fuentes ............... A61M 25/005 604/95.04 |
| 2013/0012925 A1 | 1/2013 | Berthiaume et al. |

* cited by examiner

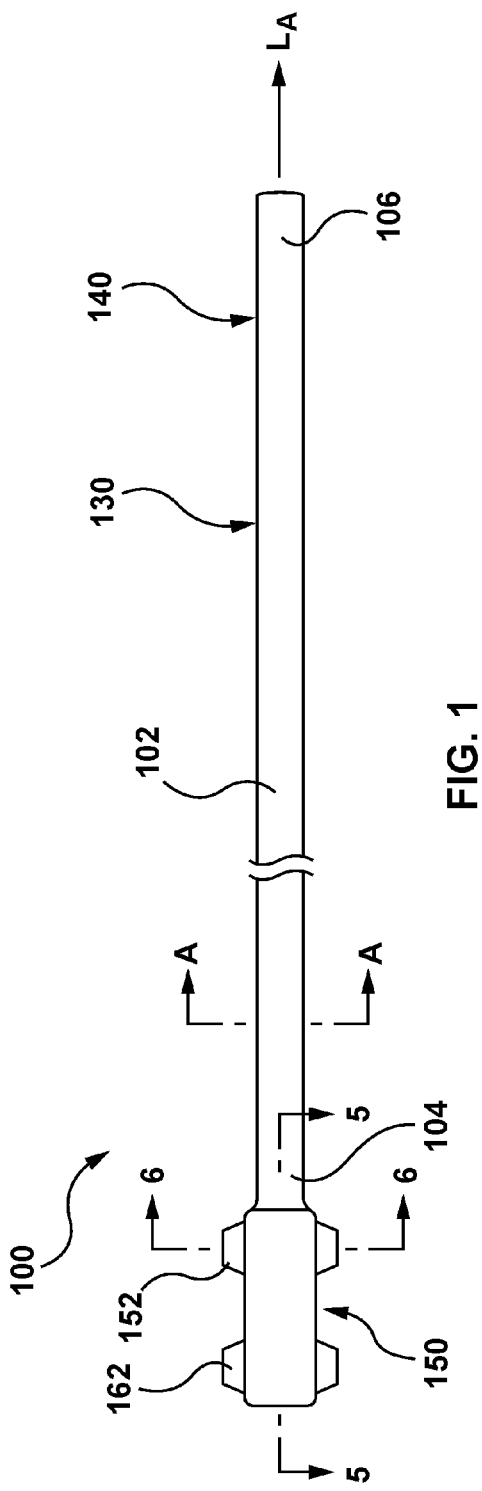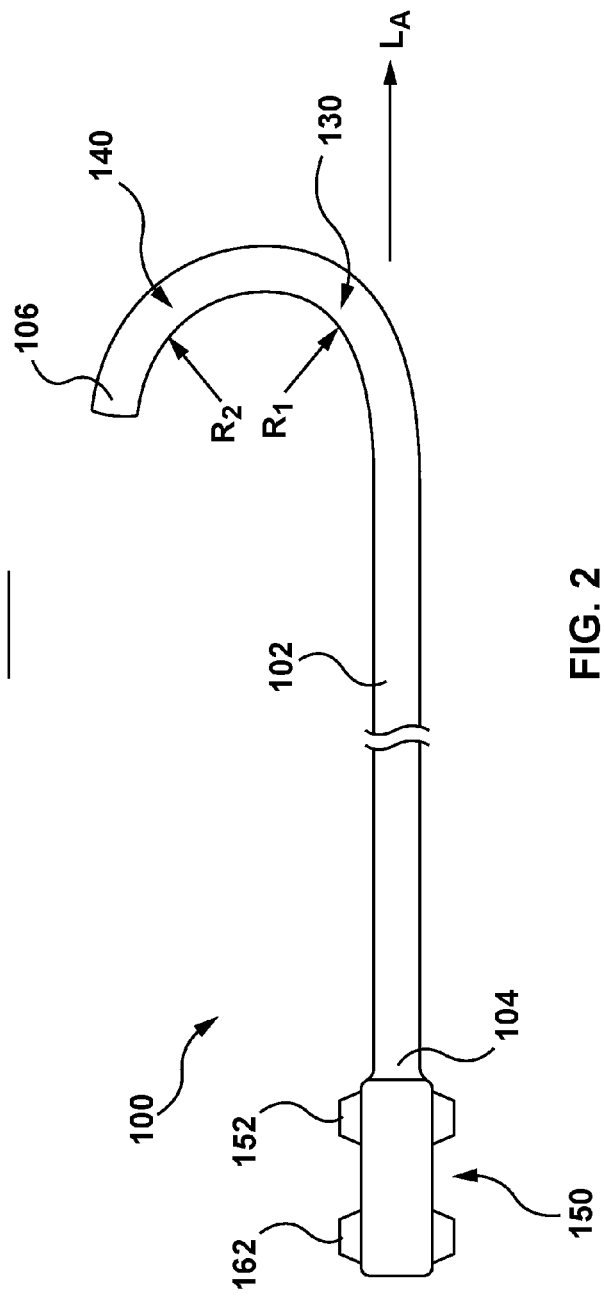
FIG. 1
FIG. 2

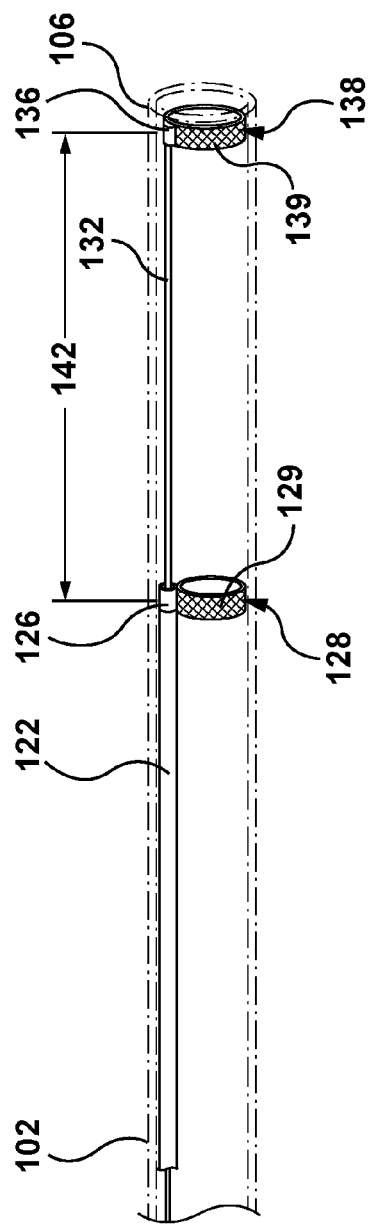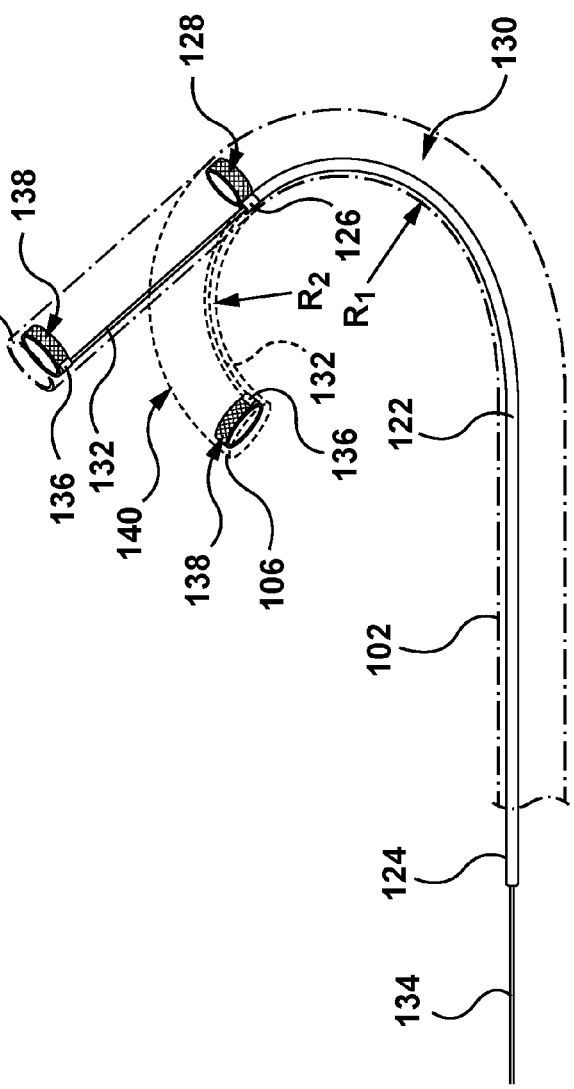

STEERABLE CATHETER WITH MULTIPLE BENDING RADII VIA A STEERING MECHANISM WITH TELESCOPING TUBULAR COMPONENTS

FIELD OF THE INVENTION

The invention relates generally to catheters, and in particular to catheters that may be selectively steered or bent in situ.

BACKGROUND OF THE INVENTION

A variety of catheters for delivering a therapy and/or monitoring a physiological condition have been implanted or proposed for implantation in patients. Catheters may deliver therapy to, and/or monitor conditions associated with, the heart, muscle, nerve, brain, stomach or other organs or tissue. Many catheters are tracked through the vasculature to locate a therapeutic or diagnostic portion of the catheter at a target site. Such catheters must have flexibility to navigate the twists and turns of the vasculature, sufficient stiffness in the proximal portion thereof to be pushed through the vasculature alone or over a guidewire or through a lumen, and the capability of orienting a distal portion thereof in alignment with an anatomical feature at the target site so that a diagnostic or therapeutic procedure can be completed. In general terms, the catheter body must also resist kinking and be capable of being advanced through access pathways that twist and turn, sometimes abruptly at acute angles.

For certain procedures, it may be necessary for the clinician to accurately steer or deflect the catheter so that a distal opening thereof may be aligned with an ostium of a branch or side vessel. The distal portions of catheters frequently need to be selectively curved or bent and straightened again while being advanced within the patient to steer the catheter distal end into a desired body lumen or chamber. For example, it may be necessary to direct the catheter distal end through tortuous anatomies and/or into a branch at a vessel bifurcation. In addition, some procedures require high accuracy in guidewire orientation. For example, often patient's arteries are irregularly shaped, highly tortuous and very narrow. The tortuous configuration of the arteries may present difficulties to a clinician in advancement of a catheter to a treatment site.

It is known to employ a pull wire connected to a distal portion of certain catheters and controlled by a proximal handle component. With such mechanisms, when the pull wire is pulled, the catheter is bent or deflected in the direction of the pulled wire. However, a need in the art still generally exists for improved apparatuses and methods for navigating through or within a patient's anatomy.

BRIEF SUMMARY OF THE INVENTION

Embodiments hereof relate to a steerable catheter including a tubular sheath having a lumen formed within a wall thereof, and a steering mechanism disposed within the lumen. The steering mechanism includes first and second steering components. At least a segment of the second steering component is coaxially disposed within the first steering component. The first steering component and the second steering component are separately tensioned to bend respective regions of the tubular sheath.

According to another embodiment hereof, a steerable guide catheter includes a tubular sheath defining a central lumen sized to receive a medical device there-through. A longitudinally-extending lumen is formed with a wall of the tubular sheath. A pull tube defines a pull wire lumen, the pull tube having a distal end attached at a first anchor point to the tubular sheath and having at least a segment slidably disposed within the longitudinally-extending lumen of the tubular sheath. A pull wire has a distal end attached at a second anchor point to the tubular sheath and having at least a segment slidably disposed within the pull wire lumen of the pull tube. The second anchor point is distal of the first anchor point. The pull tube and the pull wire are separately tensioned to bend respective regions of the tubular sheath.

According to another embodiment hereof, a steerable delivery system for a prosthesis includes a tubular sheath defining a central lumen and having a lumen formed within a wall thereof, a pull tube having at least a segment slidably disposed in the lumen within the wall of the tubular sheath, and a pull wire having at least a segment slidably disposed within the pull tube. A distal end of the pull tube is attached at a first anchor point to the tubular sheath and a distal end of the pull wire is attached at a second anchor point to the tubular sheath and wherein the second anchor point is distal of the first anchor point. The pull tube and the pull wire are separately tensioned to bend respective regions of the tubular sheath.

BRIEF DESCRIPTION OF DRAWINGS

The foregoing and other features and advantages of the invention will be apparent from the following description of embodiments thereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 1 is a side view of a tubular sheath according to an embodiment hereof, wherein a distal section of the tubular sheath is in a straight configuration.

FIG. 2 is a side view of the tubular sheath of FIG. 1, wherein the distal section of the tubular sheath includes a proximal portion and a distal portion and the proximal portion is curved to a first radius of curvature and the distal portion of the tubular sheath is curved to a second radius of curvature.

FIG. 3 is a perspective illustration of the tubular sheath of FIG. 1, wherein the distal section of the tubular sheath is in a straight configuration.

FIG. 4 is a perspective illustration of the tubular sheath of FIG. 1, wherein the distal section of the tubular sheath includes a proximal portion and a distal portion and the proximal portion is curved to a first radius of curvature and the distal portion of the tubular sheath is curved to a second radius of curvature.

DETAILED DESCRIPTION OF THE INVENTION

Figure 1B:
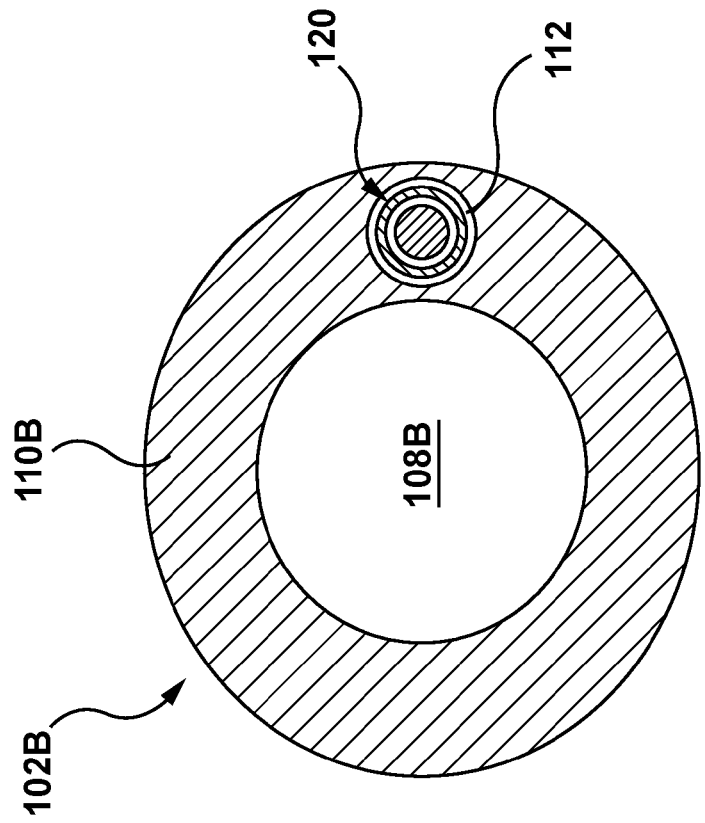
FIG. 1B is a cross-sectional view of a tubular sheath according to another embodiment hereof, wherein the sidewall thereof has a non-varying or constant thickness.

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

The following detailed description is merely exemplary in nature and is not intended to limit the invention or the application and uses of the invention. Although the description of the invention is in the context of treatment of heart valves, the invention may also be used where it is deemed useful in endoscopic procedures, procedures in the coronary vessels, or procedures in the peripheral vessels. Furthermore, there is no intention to be bound by any expressed or implied theory presented in the preceding technical field, background, brief summary or the following detailed description.

Embodiments hereof relate to catheters or similar apparatuses having multiple steerable portions that may be selectively and individually bent in situ. More particularly, with reference to FIGS. 1-4, embodiments hereof relate to a steerable catheter 100 including a tubular component or sheath 102 and a handle 150 coupled to a proximal end 104 of tubular sheath 102 to allow for steering of tubular sheath 102 as described herein. Tubular sheath 102 has a distal end 106 opposite handle 150. FIG. 1 and FIG. 3 are side and perspective views, respectively, of steerable catheter 100 in a straight or straightened configuration, while FIG. 2 and FIG. 4 are side and perspective views, respectively, of steerable catheter 100 in a curved or bent configuration in which a proximal steering region or portion 130 of tubular sheath 102 is curved to a first radius of curvature $R_1$ and a distal steerable portion 140 of tubular sheath 102 is curved to a second radius of curvature $R_2$. As will be explained in more detail herein, steerable catheter 100 has a steering mechanism 120 for controllably steering proximal steerable portion 130 of tubular sheath 102 and distal steerable portion 140 of tubular sheath 102. Steering mechanism 120 is accessible to a user via handle 150 and is configured to separately or individually bend or deflect proximal and distal steerable portions 130, 140 of tubular sheath 102. Stated another way, proximal and distal steerable portions 130, 140 of tubular sheath 102 are steerable portions of the tubular sheath in that the curvature thereof can be changed based on the user manipulating steering mechanism 120 via handle 150.

Figure 1A:
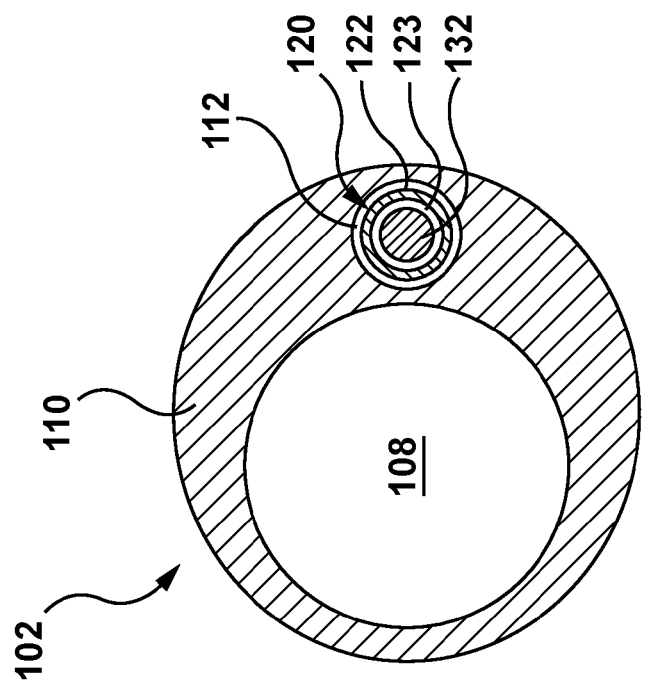
FIG. 1A is a cross-sectional view of the tubular sheath of FIG. 1 taken along line A-A of FIG. 1.

As best shown on FIG. 1A, which is a cross-sectional view of tubular sheath 102 of FIG. 1 taken along line A-A of FIG. 1, tubular sheath 102 defines a central lumen 108 extending there-through, i.e., from proximal end 104 to distal end 106 thereof, and a longitudinally-extending lumen 112 is formed with a wall 110 of tubular sheath 102. In an embodiment, longitudinally-extending lumen 112 is pre-formed in wall 110 of tubular sheath 102 and may be formed for example by multi-lumen profile extrusion. Central lumen 108 is open at distal end 106 of tubular sheath 102 which in turn forms the distal end of steerable catheter 100. Longitudinally-extending lumen 112 extends adjacent or parallel to central lumen 108. However, longitudinally-extending lumen 112 does not extend the entire length of tubular sheath 102 but terminates proximal to distal end 106 of tubular sheath 102. Longitudinally-extending lumen 112 houses steering mechanism 120. In an embodiment hereof, as will be explained in more detail herein, central lumen 108 is sized or configured to slidingly receive a medical device such as a guidewire or a treatment catheter there-through when steerable catheter 100 is configured to be an introducer or guide catheter. In another embodiment hereof, as will be explained in more detail herein, central lumen 108 is sized or configured to house an inner shaft component when steerable catheter 100 is configured to be an outer component of a treatment or delivery catheter. Stated another way, in an embodiment hereof, steerable catheter 100 is a standalone catheter while in another embodiment hereof, steerable catheter 100 forms an outer component of medical device such as but not limited to a treatment or delivery catheter.

In the embodiment of FIG. 1A, wall 110 has a variable thickness such that the thickness of tubular sheath 102 is greater along one side thereof to accommodate longitudinally-extending lumen 112 formed there-through. The variable thickness of wall 110 minimizes the overall profile of tubular sheath 102. However, tubular sheath 102 and wall 110 may have other configurations such as but not limited to the configuration shown in FIG. 1B. FIG. 1B is a cross-sectional view of a tubular sheath 102B according to another embodiment hereof. Tubular sheath 102B defines a central lumen 108B extending there-through and a longitudinally-extending lumen 112B is formed with a wall 110B of tubular sheath 102B. Wall 110B has a non-varying or constant thickness, the thickness being sufficient to accommodate longitudinally-extending lumen 112B and steering mechanism 120 coaxially disposed therein.

In addition, although depicted as circular, longitudinally-extending lumen 112 as well as steering mechanism 120 disposed there-through may have different configurations or shapes. For example, in another embodiment hereof, longitudinally-extending lumen 112 may have an oval or oblong cross-section and the tubular components of steering mechanism 120, e.g., pull tube 122 and pull wire 132, may each have an oval or oblong cross-section and a flat or flattened longitudinal profile.

Steering mechanism 120 is coaxially disposed within longitudinally-extending lumen 112 of tubular sheath 102. Steering mechanism 120 includes a first steering component or pull tube 122 and a second steering component or pull wire 132 which is coaxially disposed within a lumen 123 defined by pull tube 122. Pull tube 122 may also be considered an exterior tube or tubular component that forms a slidable lumen while pull wire 132 is an interior tube or tubular component slidably disposed within pull tube 122. As used herein, "slidably" denotes back and forth movement in a longitudinal direction along longitudinal axis $L_A$ of steering catheter 100. Pull wire 132 nests or telescopes within pull tube 122 so that the overall profile of steering catheter 100 is reduced compared to steering components that are disposed parallel to each other. In an embodiment hereof, pull tube 122 is a hypotube. Pull tube 122 and pull wire 132 may be separately controlled or manipulated to cause a particular or respective portion of tubular sheath 102 to bend or curve in a curling motion. While pull tube 122 and pull wire 132 are primarily housed or disposed within longitudinally-extending lumen 112 of tubular sheath 102, proximal ends 124, 134, respectively, proximally extend beyond proximal end 104 of tubular sheath 102 and are accessible via handle 150 to be pulled or pushed which results in controlled bending movement of the corresponding steerable portion of tubular sheath 102.

More particularly, pull tube 122 includes at least a segment slidably disposed within longitudinally-extending lumen 122 of tubular sheath 102. Proximal end 124 of pull tube 122 is attached or coupled to a first actuator 152 of handle 150 as shown on FIG. 5 and a distal end 126 of pull tube 122 is attached or coupled to tubular sheath 102 at a first anchor point 128 as shown on FIG. 3. First actuator 152 will be described in more detail below with reference to FIGS. 5 and 6. First anchor point 128 is proximally spaced from distal end 106 of tubular sheath 102 such that tensioning or pulling of pull tube 122 via first actuator 152 bends or curves proximal steerable portion 130 to a first radius of curvature $R_1$ as shown on FIGS. 2 and 4. The dimension of first radius of curvature $R_1$ depends upon the intended application of steerable catheter 100, the target anatomy for use of steerable catheter 100, and/or the size or profile of steerable catheter 100. In an embodiment in which steerable catheter 100 is utilized in a TAVI or transcatheter aortic valve implantation procedure, first radius of curvature $R_1$ ranges between thirty five (35) millimeters and eighty (80) millimeters. In another embodiment hereof in which steerable catheter 100 is utilized in neurological applications, first radius of curvature $R_1$ may be as small as 0.5 centimeters. Distal end 126 of pull tube 122 is attached or fixed to tubular sheath 102 within longitudinally-extending lumen 122 thereof. In an embodiment depicted herein, pull tube 122 is formed from stainless steel and a metal band or ring 129 is utilized to attach distal end 126 of pull tube 122 to tubular sheath 102. Distal end 126 of pull tube 122 is attached to metal band 129 by welding. In another embodiment hereof, pull tube 122 is formed from a relatively hard polymeric material, with high tensile stiffness, and the polymer material of distal end 126 is reflowed in order to attach distal end 126 of pull tube 122 to tubular sheath 102. Distal end 126 of pull tube 122 may alternatively be attached to tubular sheath 102 using other conventional techniques, including bonding or adhesive, and it will be understood by one of ordinary skill in the art that the method of attachment depends upon the material of pull tube 122.

Tubular sheath 102 may be formed of one or more polymeric materials, non-exhaustive examples of which include polyethylene, polyethylene block amide copolymer (PEBA), polyamide and/or combinations thereof, either laminated, blended or co-extruded. Optionally, tubular sheath 102 or some portion thereof may be formed as a composite having a reinforcement layer incorporated within a polymeric body in order to enhance strength and/or flexibility and/or torquability. Suitable reinforcement layers include braiding, wire mesh layers, embedded axial wires, embedded helical or circumferential wires, hypotubes, and the like. In one embodiment, for example, at least a proximal portion of tubular sheath 102 may be formed from a reinforced polymeric tube. In an embodiment hereof, tubular sheath 102 may include articulated longitudinal sections corresponding to the first and second radii of curvature $R_1$, $R_2$ and the articulated longitudinal sections are formed from different polymers to each other and/or to the main proximal section thereof.

Pull wire 132 includes at least a segment slidably disposed within lumen 123 of pull tube 122. Proximal end 134 of pull wire 132 is attached or coupled to a second actuator 162 of handle 150 as shown on FIG. 5 and a distal end 136 of pull wire 132 is attached or coupled to tubular sheath 102 at a second anchor point 138 as shown on FIG. 3. Second actuator 162 will be described in more detail below with reference to FIGS. 5 and 6. Second anchor point 138 is distal of first anchor point 128. In an embodiment, second anchor point 138 is at distal end 106 of tubular sheath 102 such that tensioning or pulling of pull wire 132 via second actuator 162 bends or curves distal steerable portion 140 to a second radius of curvature $R_2$ as shown on FIGS. 2 and 4. The dimension of second radius of curvature $R_2$ depends upon the intended application of steerable catheter 100, the target anatomy for use of steerable catheter 100, and/or the size or profile of steerable catheter 100. In an embodiment in which steerable catheter 100 is utilized in a TAVI or transcatheter aortic valve implantation procedure, second radius of curvature $R_2$ ranges between twenty (20) millimeters and sixty (60) millimeters. In another embodiment hereof in which steerable catheter 100 is utilized in neurological applications, second radius of curvature $R_2$ may be as small as 0.5 centimeters. As best shown on FIG. 3, a distal segment 142 of pull wire 132 extends from distal end 126 of pull tube 122 to second anchor point 138 and is slidably disposed within a corresponding distal portion of longitudinally-extending lumen 112 of tubular sheath 102. In an embodiment depicted herein, pull wire 132 is formed from stainless steel and a metal band or ring 139 is utilized to attach distal end 136 of pull wire 132 to tubular sheath 102. Distal end 136 of pull wire 132 is attached to metal band 139 by welding. In another embodiment hereof, pull wire 132 is formed from KEVLAR or another relatively hard polymeric material and the polymer material of distal end 136 is reflowed in order to attach distal end 136 of pull wire 132 to tubular sheath 102. Distal end 136 of pull wire 132 may alternatively be attached to tubular sheath 102 using other conventional techniques, including bonding or adhesive, and it will be understood by one of ordinary skill in the art that the method of attachment depends upon the material of pull wire 132. Pull wire 132 and pull tube 122 may be formed from different materials and thus the method of attachment for pull wire 132 and pull tube 122 may differ.

With pull tube 122 and pull wire 132 attached to tubular sheath 102 at spaced apart locations or anchor points, pull tube 122 and pull wire 132 are configured to be separately and individually tensioned to bend or deflect respective steerable regions of tubular sheath 102, namely proximal steerable portion 130 and distal steerable portion 140, respectively. Proximal steerable portion 130 is proximal of distal end 126 of pull tube 122 and distal steerable portion 140 is distal of distal end 126 of pull tube 122. Tensioning of pull tube 122 bends proximal steerable portion 130 to first radius of curvature $R_1$, while tensioning of pull wire 132 bends distal steerable portion 140 to second radius of curvature $R_2$. In an embodiment, the first and second radii of curvature $R_1$, $R_2$ are different from each other. The ability to individually or separately bend two regions of tubular sheath 102 provides a number of advantages. For example, steerable catheter 100 may better conform to the anatomy of a heart or vasculature that is encountered during a surgical procedure. The distance between first anchor point 128 of pull tube 122 and second anchor point 138 of pull wire 132 depends upon the intended application of steerable catheter 100, the target anatomy for use of steerable catheter 100, and/or the size or profile of steerable catheter 100. In an embodiment hereof in which steerable catheter 100 is utilized in a TAVI or transcatheter aortic valve implantation procedure, the distance between first anchor point 128 of pull tube 122 and second anchor point 138 of pull wire 132 ranges between five (5) and eight (8) centimeters. In another embodiment hereof in which steerable catheter 100 is utilized in neurological applications and thus has a relatively smaller profile, the first and second anchor points are relatively closer together. The coaxial configuration of pull tube 122 and pull wire 132 allows the two respective radii of curvature, i.e., first radius of curvature $R_1$ and second radius of curvature $R_2$, to form in the same plane. If the two steering mechanisms are disposed parallel to each other but not coaxial, an offset pulls one radii out of plane with respect to the other.

Figure 5:
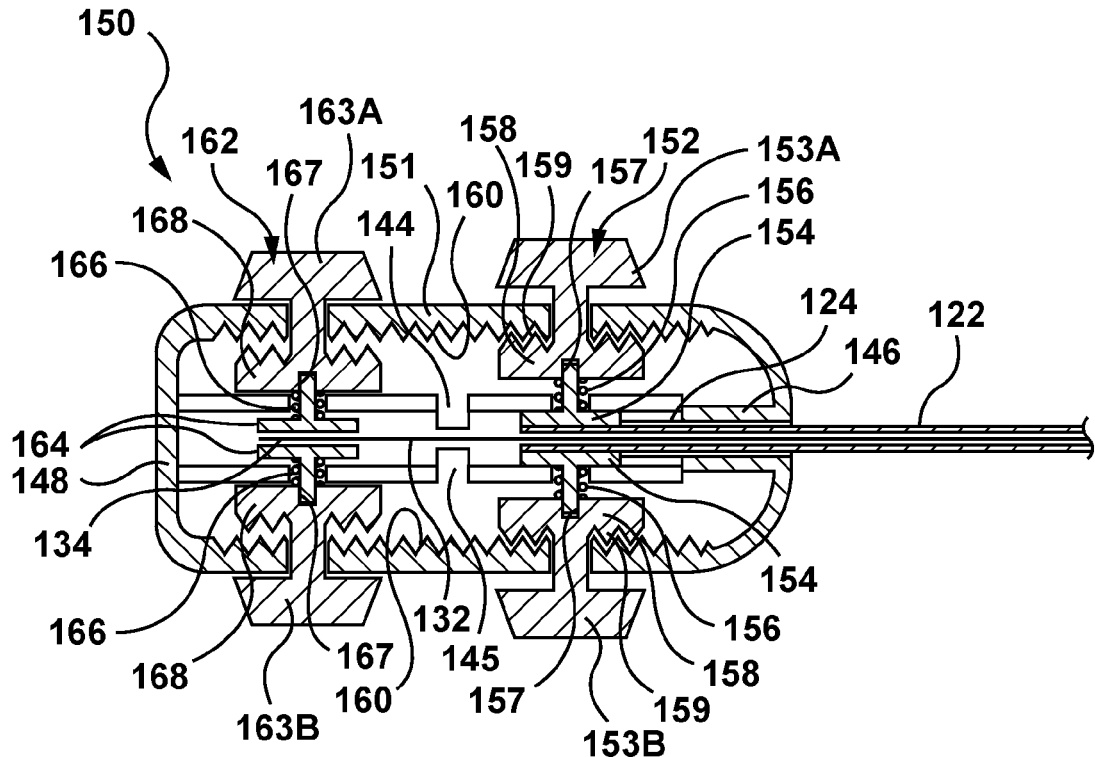
FIG. 5 is a sectional view of a handle of the tubular sheath of FIG. 1 taken along line 5-5 of FIG. 1.
Figure 6:
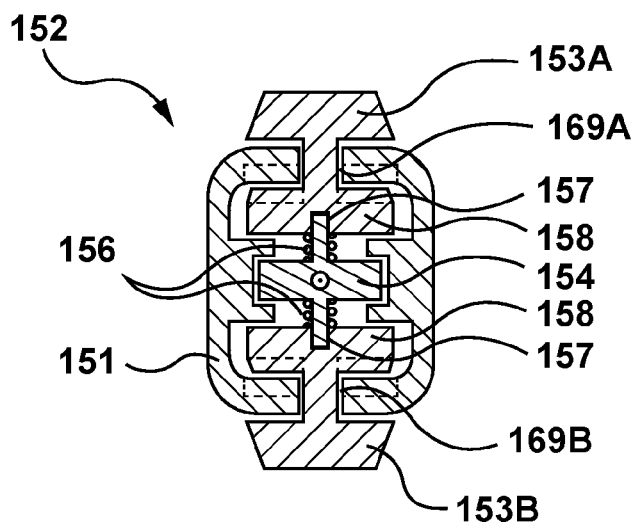
FIG. 6 is a cross-sectional view of the handle of the tubular sheath of FIG. 1 taken along line 6-6 of FIG. 1.

With reference to FIGS. 5 and 6, handle 150 having first and second actuators 152, 162 for selectively controlling pull tube 122 and pull wire 132, respectively, and thereby selectively bending or deflecting proximal steerable portion 130 and distal steerable portion 140, respectively, of tubular sheath 102 is described in more detail. FIG. 5 is a sectional view taken along line 5-5 of FIG. 1, and FIG. 6 is a cross-sectional view taken along line 6-6 of FIG. 1. First actuator 152 is operably coupled to proximal end 124 of pull tube 122, while second actuator 162 is operably coupled to proximal end 134 of pull wire 132. First actuator 152 includes opposing buttons or buttons 153A, 153B, a pair of locking mechanisms 158, a pair of springs 156, and a clamp 154, while second actuator 162 similarly includes opposing grips or buttons 163A, 163B, a pair of locking mechanisms 168, a pair of springs 166, and a clamp 164. Handle 150 includes a handle body 151 with a generally cylindrical hollow shape or configuration to house or receive the working components of handle 150. Longitudinal slots 169A, 169B (shown on FIG. 6) are formed along opposing top and bottom surfaces of handle body 151 to allow buttons 153A, 153B of first actuator 152 and buttons 163A, 163B of second actuator 162 to extend there-through and be accessible to an operator or user. Buttons 153A, 153B of first actuator 152 and buttons 163A, 163B of second actuator 162 are moved longitudinally or linearly, i.e., forward and backward, within longitudinal slots 169A, 169B to cause movement of pull tube 122 and pull wire 132, respectively.

First actuator 152 operably coupled to proximal end 124 of pull tube 122 will first be described. Each grip or button 153A, 153B of first actuator 152 includes a post or protrusion that extends inwardly from an inner surface thereof through longitudinal slots 169A, 169B formed along opposing top and bottom surfaces of handle body 151. Attached to or integrally formed with each post or protrusion is a locking mechanism 158 having outwardly-extending teeth 159 formed along an outer surface thereof. Outwardly-extending teeth 159 mate or interlock with inwardly-extending teeth 160 formed on an inner surface of handle body 151. Locking mechanisms 158 further include a recess or groove 157 formed on an inner surface thereof. A portion of clamp 154 is housed within recesses 157 of locking mechanisms 158 and clamp 154 is further attached or fixed to proximal end 124 of pull tube 122. Springs 156 extend between clamp 154 and each locking mechanism 158.

In operation, first actuator 152 is normally in a locked position in which springs 156 outwardly bias or push locking mechanisms 158 radially outward such that outwardly-extending teeth 159 of locking mechanism mate or interlock with inwardly-extending teeth 160 of handle body 151. When outwardly-extending teeth 159 mate or interlock with inwardly-extending teeth 160, first actuator 152 and thus pull tube 122 are in a locked position and cannot be moved by the operator. When it is desired to apply tension or release tension to pull tube 122, the operator first inwardly presses or pushes buttons 153A, 153B of first actuator 152 in order to disengage outwardly-extending teeth 159 from inwardly-extending teeth 160. When the operator inwardly presses or pushes buttons 153A, 153B of first actuator 152, springs 156 are compressed and a portion of clamp 154 extends into or extends further into recesses 157 of locking mechanisms 158. When outwardly-extending teeth 159 are disengaged from inwardly-extending teeth 160, buttons 153A, 153B, locking mechanisms 158, and clamp 154 are free to move as a single unit that is attached to pull tube 122 and thereby moves pull tube 122 as well. Thus, with buttons 153A, 153B of first actuator 152 still pressed or pushed inward, the operator may slide or move pull tube 122 backward, e.g., in a proximal direction, in order to apply tension to tubular sheath 102 and thus bend or increase bending of proximal steerable portion 130 thereof and/or the operator may slide or move pull tube 122 forward, e.g., in a distal direction, in order to release tension to tubular sheath 102 and thus straighten or decrease bending of proximal steerable portion 130 thereof. Longitudinal movement of first actuator 152 is limited or constrained via stoppers 144, 145 formed within handle body 151 as well as by a distal end 146 of handle body 151. When buttons 153A, 153B are released by the user, springs 156 return to their normal or uncompressed configuration and outwardly bias or push locking mechanisms 158 radially outward such that outwardly-extending teeth 159 of locking mechanisms 158 mate or interlock with inwardly-extending teeth 160 of handle body 151. As such, when buttons 153A, 153B are released by the user, first actuator 152 resumes its locked configuration which is the normal or rest configuration of first actuator 152 without any forces applied thereto.

Second actuator 162 is operably coupled to proximal end 134 of pull wire 132 and operates similar to first actuator 152. More particularly, each grip or button 163A, 163B of second actuator 162 includes a post or protrusion that extends inwardly from an inner surface thereof through longitudinal slots 169A, 169B formed along opposing top and bottom surfaces of handle body 151. Attached to or integrally formed with each post or protrusion is a locking mechanism 168 having outwardly-extending teeth 169 formed along an outer surface thereof. Outwardly-extending teeth 169 mate or interlock with inwardly-extending teeth 160 formed on an inner surface of handle body 151. Locking mechanisms 168 further includes a recess or groove 167 formed on an inner surface thereof. A portion of clamp 164 is housed within recesses 167 of locking mechanisms 168 and clamp 164 is further attached or fixed to proximal end 134 of pull wire 132. Springs 166 extend between clamp 164 and each locking mechanism 168.

In operation, second actuator 162 is normally in a locked position in which springs 166 outwardly bias or push locking mechanism 168 radially outward such that outwardly-extending teeth 169 of locking mechanism mate or interlock with inwardly-extending teeth 160 of handle body 151. When outwardly-extending teeth 169 mate or interlock with inwardly-extending teeth 160, second actuator 162 and thus pull wire 132 are in a locked position and cannot be moved by the operator. When it is desired to apply tension or release tension to pull wire 132, the operator first inwardly presses or pushes buttons 163A, 163B of second actuator 162 in order to disengage outwardly-extending teeth 169 from inwardly-extending teeth 160. When the operator inwardly presses or pushes buttons 163A, 163B of second actuator 162, springs 166 are compressed and a portion of clamp 164 extends into or extends further into recesses 167 of locking mechanisms 168. When outwardly-extending teeth 169 are disengaged from inwardly-extending teeth 160, buttons 163A, 163B, locking mechanisms 168, and clamp 164 are free to move as a single unit that is attached to pull wire 132 and thereby moves pull wire 132 as well. Thus, with buttons 163A, 163B of second actuator 162 still pressed or pushed inward, the operator may slide or move pull wire 132 backward, e.g., in a proximal direction, in order to apply tension to tubular sheath 102 and thus bend or increase bending of proximal steerable portion 130 thereof and/or the operator may slide or move pull wire 132 forward, e.g., in a distal direction, in order to release tension to tubular sheath 102 and thus straighten or decrease bending of proximal steerable portion 130 thereof. Longitudinal movement of second actuator 162 is limited or constrained via stoppers 144, 145 formed within handle body 151 as well as by a proximal end 148 of handle body 151. When buttons 163A, 163B are released by the user, springs 166 return to their normal or uncompressed configuration and outwardly bias or push locking mechanisms 168 radially outward such that outwardly-extending teeth 169 of locking mechanisms 168 mate or interlock with inwardly-extending teeth 160 of handle body 151. As such, when buttons 163A, 163B are released by the user, second actuator 162 resumes its locked configuration which is the normal or rest configuration of second actuator 162 without any forces applied thereto.

Tubular sheath 102 may be formed of polymeric materials, non-exhaustive examples of which include polyethylene terephthalate (PET), polypropylene, polyethylene, polyether block amide copolymer (PEBA), polyamide, fluoropolymers, and/or combinations thereof, either laminated, blended or co-extruded. Optionally, tubular sheath 102 or some portion thereof may be formed as a composite having a reinforcement layer incorporated within a polymeric body in order to enhance strength and/or flexibility. Suitable reinforcement layers include braiding, wire mesh layers, embedded axial wires, embedded helical or circumferential wires, hypotubes, and the like. In one embodiment, for example, at least a proximal portion of tubular sheath 102 may be formed from a reinforced polymeric tube.

Figure 7:
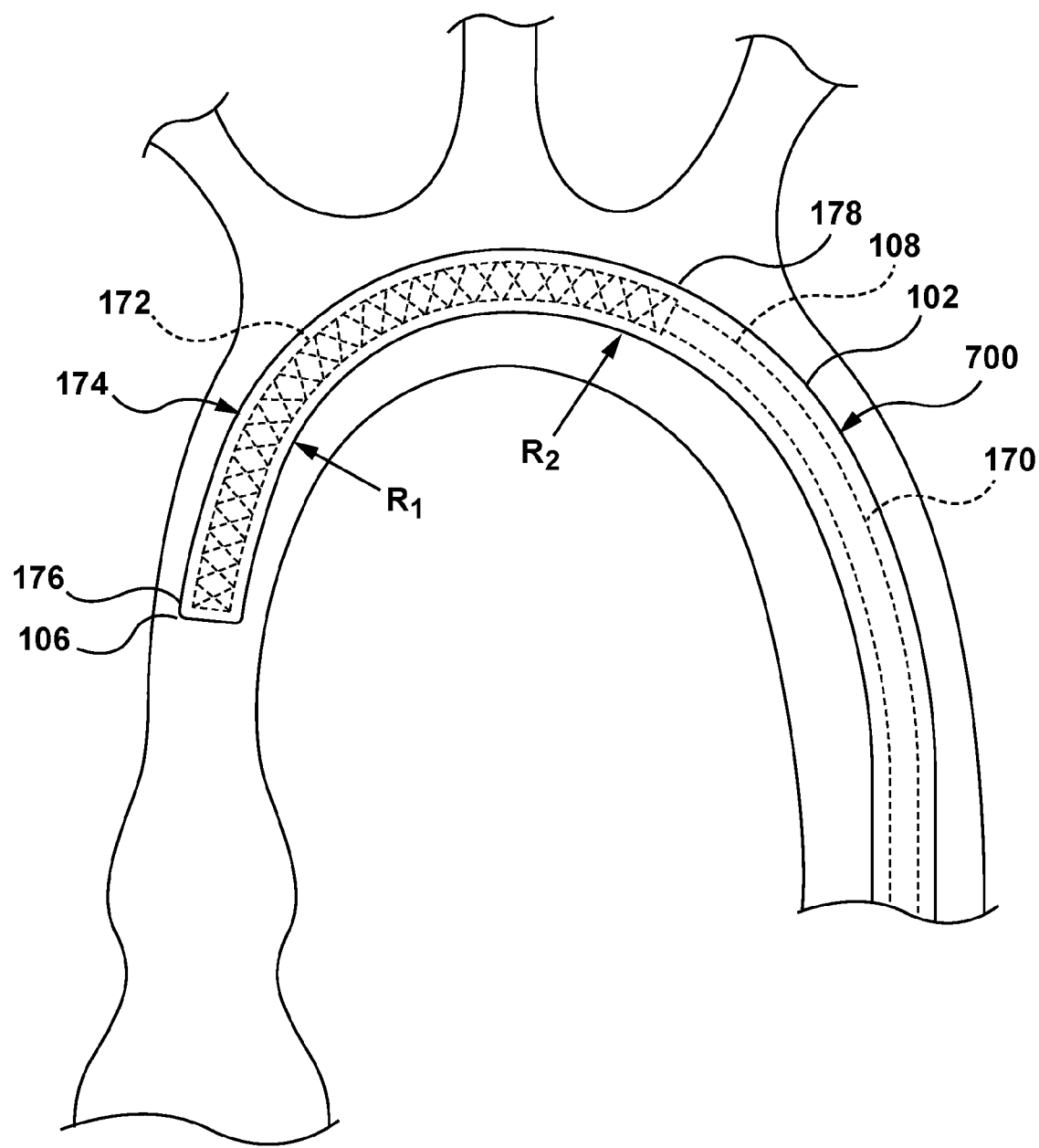
FIG. 7 is a side view of a distal portion of a delivery catheter including the tubular sheath of FIG. 1, wherein the delivery catheter is being delivered in situ to an aortic valve.

As previously mentioned, in an embodiment hereof, steerable catheter 100 may form an outer component of medical device such as but not limited to a treatment or delivery catheter. FIG. 7 is a side view of a distal portion of a steerable delivery catheter 700 including tubular sheath 102 which forms an outer component of delivery catheter 700. In FIG. 7, steerable delivery catheter 700 is shown in situ to an aortic valve and is utilized for delivering a self-expanding heart valve prosthesis 172. Steerable delivery catheter 700 is configured for endoluminal transcatheter repair/replacement of a defective heart valve, and in particular is configured for a TAVI or transcatheter aortic valve implantation procedure. Heart valve prosthesis 172 is mounted over a distal portion of an inner shaft component 170 of steerable delivery catheter 700, and central lumen 108 of tubular sheath 102 is sized or configured to slidingly receive inner shaft component 170. Steerable delivery catheter 700 is depicted in a delivery configuration in FIG. 7 with heart valve prosthesis 172 loaded within a distal portion 174 of steerable delivery catheter 700. Distal portion 174 of tubular sheath 102 is configured to hold heart valve prosthesis 172 in a compressed, delivery configuration as shown in FIG. 7. In the delivery configuration, distal portion 174 of tubular sheath 102 is disposed over heart valve prosthesis 172 to compressively retain the heart valve prosthesis in crimped engagement with inner shaft component 170. In an embodiment, distal portion 174 is an integral or continuous portion or section of tubular sheath 102. However, in another embodiment, distal portion 174 is a capsule component and is formed as a separate component from tubular sheath 102 as described in U.S. Patent Publication No. 2011/0245917 to Savage et al., U.S. Patent Publication No. 2011/0251675 to Dwork, U.S. Patent Publication No. 2011/0251681 to Shipley et al., U.S. Patent Publication No. 2011/0251682 to Murray, III et al., and/or U.S. Patent Publication No. 2011/0264202 to Murray, III et al., each of which is herein incorporated by reference in its entirety.

Distal portion 174 may be considered to have a proximal end 178 and a distal end 176. In an embodiment hereof, first anchor point 128 of pull tube 122 is positioned at proximal end 178 of distal portion 174 of tubular sheath 102 and second anchor point 138 of pull wire 132 is at distal end 176 of distal portion 174. Distal end 176 of distal portion 174 forms or is at distal end 106 of tubular sheath 102. When distal portion 174 is a capsule component, first anchor point 128 of pull tube 122 is positioned proximal to the capsule and second anchor point 138 of pull wire 132 is at a distal end of the capsule. When being delivered to the aortic valve, tubular sheath 102 bends or curves at two distinct radii, i.e., first radius of curvature $R_1$ and second radius of curvature $R_2$, in order to conform to the shape of the aortic arch. Although shown and described in use with a self-expanding heart valve prosthesis, tubular sheath 102 may be used with a variety of catheters including but not limited to a delivery catheter for a balloon-expandable heart valve prosthesis, or a delivery catheter for any type of prostheses known in the art such as prostheses configured for implantation in the coronary arteries, the peripheral arteries, or any vasculature or opening. As such, when tubular sheath 102 forms an integral outer component of a delivery catheter, tubular sheath 102 and steering assembly 120 may be considered a subassembly utilized for steering or navigating the delivery catheter through vasculature of a patient.

Figure 8:
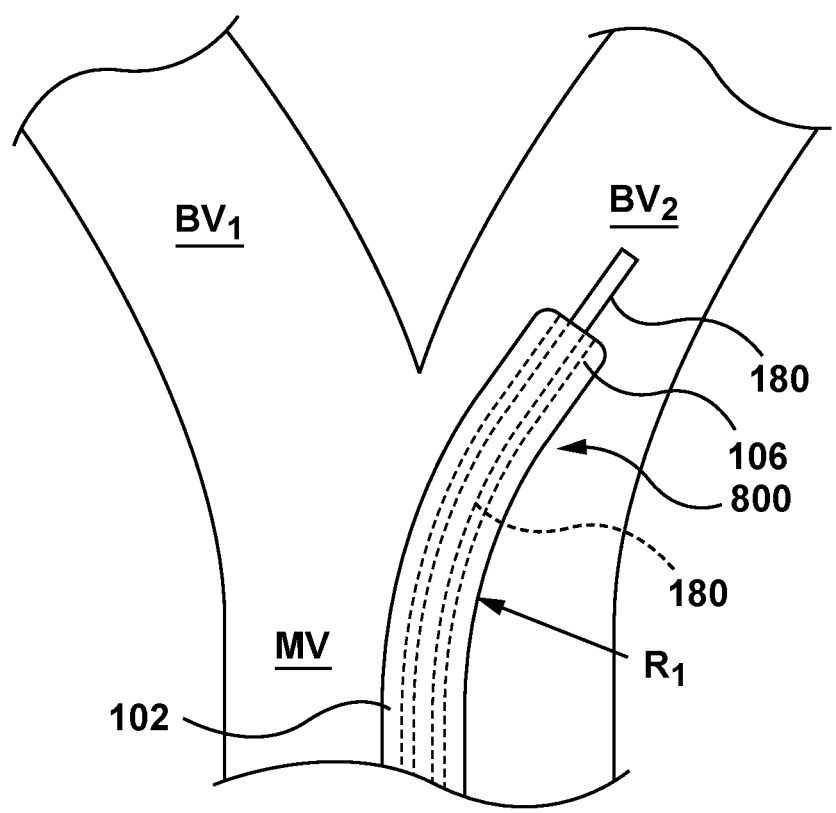
FIG. 8 is a side view of a distal portion of an introducer including the tubular sheath of FIG. 1, wherein the introducer is being delivered in situ and is positioned at a bifurcation in the vasculature.

Further, in addition to being utilized as an integral component of a delivery catheter or any other type of catheter, steerable catheter 100 may be utilized as a stand-alone guide catheter or introducer. FIG. 8 is a side view of a distal portion of an introducer or guide catheter 800 including tubular sheath 102. Guide catheter 800 may be utilized in any application in which it is desirable to orient or position a distal end of the apparatus in a direction different from that of the longitudinal axis of the apparatus, such as during navigation within a bifurcation or through tortuous anatomy. Exemplary applications include accessing the carotid, iliac or renal bifurcations, in either diagnostic or therapeutic applications. In FIG. 8, guide catheter 800 is being delivered in situ and is positioned within the vasculature at a bifurcation having a main vessel MV, a first branch vessel $BV_1$, and a second branch vessel $BV_2$. In this embodiment, central lumen 108 of tubular sheath 102 is sized or configured to slidingly receive a medical device 180 such as a guidewire or a treatment catheter there-through. When being delivered through the vasculature, tubular sheath 102 may be selectively bent or curved at two distinct radii, i.e., first radius of curvature $R_1$ and second radius of curvature $R_2$, in order to conform to the shape of the anatomy. In FIG. 8, tubular sheath 102 is only selectively bent or curved at one distinct radii, i.e., first radius of curvature $R_1$, in order to confirm to the shape of the bifurcation such that distal end 106 of tubular sheath 102 is directed towards second branch vessel $BV_2$. Medical device 180 is shown inserted through guide catheter 800 and extending into second branch vessel $BV_2$. A proximal end (not shown) of guide catheter 800 may include a touhy borst adaptor or gasket (not shown) to prevent backflow of fluids and secure the position of medical device 180 when closed as will be understood by one of ordinary skill in the art.

Figure 9:
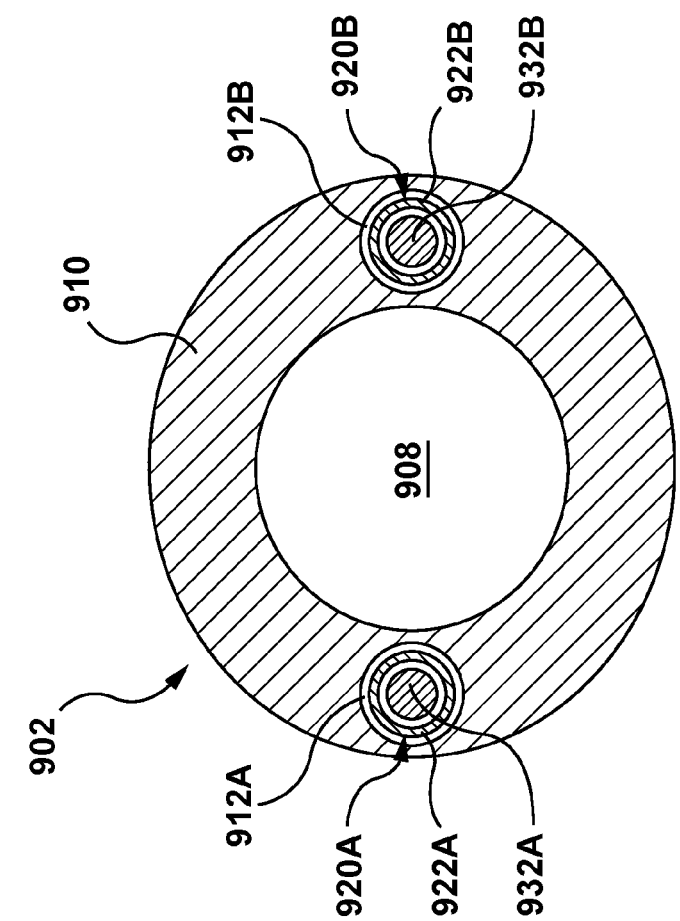
FIG. 9 is a cross-sectional view of a tubular sheath according to another embodiment hereof, wherein the tubular sheath includes a plurality of steering mechanisms at opposing sides thereof.

Although tubular sheath 102 is described above with only one steering mechanism 120, embodiments hereof may include a plurality of steering mechanisms as shown for example in FIG. 9. FIG. 9 is a cross-sectional view of a tubular sheath 902 according to another embodiment hereof. Tubular sheath 902 includes a plurality of steering mechanisms 920A, 920B at opposing sides thereof. More particularly, tubular sheath 902 defines a central lumen 908 extending there-through and two opposing longitudinally-extending lumens 912A, 912B are formed with a wall 910 of tubular sheath 902. Stated another way, longitudinally-extending lumens 912A, 912B are formed along opposing sides of tubular sheath 902. Steering mechanisms 920A, 920B are coaxially disposed within longitudinally-extending lumens 912A, 912B, respectively. Steering mechanism 920A includes a pull tube 922A and a pull wire 932A slidingly disposed within a lumen of pull tube 922A as described above with respect to pull tube 122 and pull wire 132, and steering mechanism 920B includes a pull tube 922B and a pull wire 932B slidingly disposed within a lumen of pull tube 922B as described above with respect to pull tube 122 and pull wire 132. With steering mechanisms disposed along opposing sides of tubular sheath 902, tubular sheath 902 may be selectively curved or bent in opposite directions or orientations. Although shown with only two steering mechanisms, more than two steering mechanisms may be incorporated into tubular sheath 902 in order to permit bending of tubular sheath 902 in multiple directions or planes.

Figure 10:
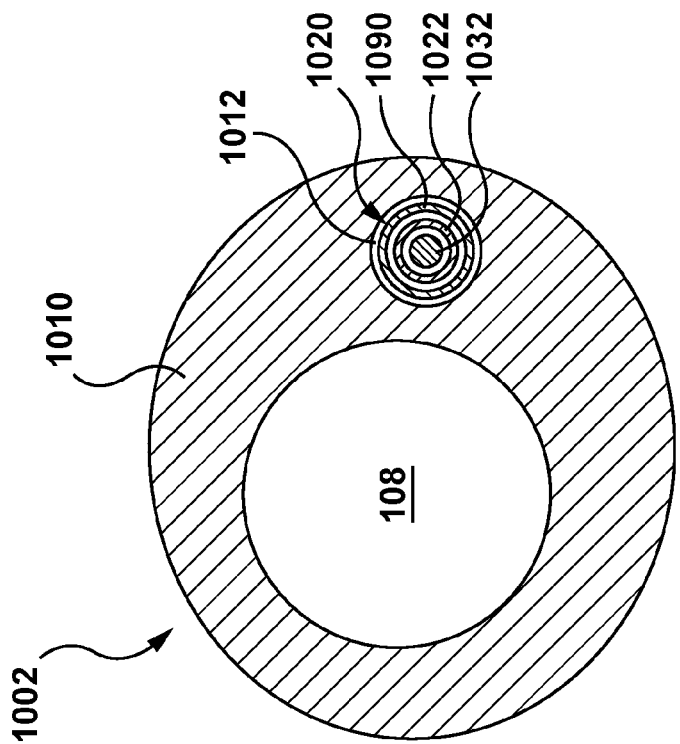
FIG. 10 is a cross-sectional view of a tubular sheath according to another embodiment hereof, wherein a steering mechanism of the tubular sheath includes three nesting or telescoping tubular sheaths.
Figure 11:
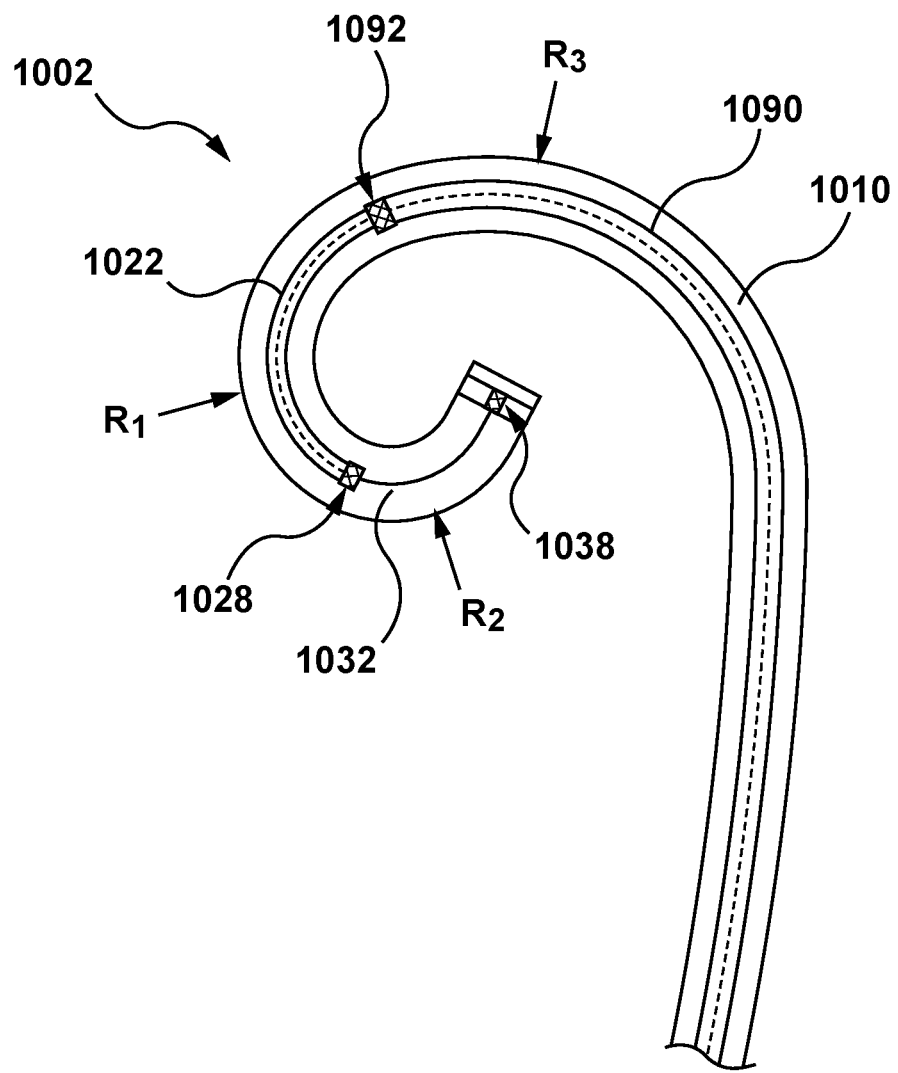
FIG. 11 is a side view of the tubular sheath of FIG. 10, wherein the distal section of the tubular sheath includes a proximal portion, an intermediate portion, and a distal portion each curved to a respective radius of curvature.

In addition, although steering mechanism 120 is described above with two telescoping or nesting components to provide two distinct steerable regions or portions of tubular sheath 102, embodiments hereof may include more than two telescoping or nesting components to provide additional distinct steerable portions of tubular sheath 102 as shown for example in FIG. 10 and FIG. 11. FIG. 10 is a cross-sectional view of a tubular sheath 1002 according to another embodiment hereof, and FIG. 11 is a side view of the tubular sheath 1002. Tubular sheath 1002 includes a steering mechanism 1020 with three nesting or telescoping tubular components. More particularly, tubular sheath 1002 defines a central lumen 1008 extending there-through and a longitudinally-extending lumen 1012 is formed with a wall 1010 of tubular sheath 1002. Steering mechanism 1020 is coaxially disposed within longitudinally-extending lumen 1012. Steering mechanism 1020 includes a pull tube 1022 and a pull wire 1032 slidingly disposed within a lumen of pull tube 1022 as described above with respect to pull tube 122 and pull wire 132. In addition, steering mechanism includes an additional or outer pull tube 1090 disposed over pull tube 1022. Stated another way, pull tube 1022 is slidingly disposed within a lumen of outer pull tube 1090. In an embodiment, outer pull tube 1090 has a third anchor point 1092 (shown in FIG. 11) which is proximal of a first anchor point 1028 (shown in FIG. 11) of pull tube 1022 which is proximal of a second anchor point 1038 (shown in FIG. 11) of pull wire 1032. Stated another way, third anchor point 1092 of outer pull tube 1090 is proximally spaced from the distal end of pull tube 1022. Tensioning or pulling of outer pull tube 1090 bends or curves another portion of tubular sheath 1002, i.e., the region or portion of tubular sheath 1002 which is adjacent to the third anchor point of outer pull tube 1090, to a third radius of curvature $R_3$ (shown in FIG. 11) which may be different from the first radius of curvature $R_1$ (shown in FIG. 11) of pull tube 1022 and/or the second radius of curvature $R_2$ (shown in FIG. 11) of pull wire 1032. Although shown with only three nesting or telescoping tubular components, more than three nesting or telescoping tubular components may be incorporated into steering mechanism 1020 in order to permit bending of tubular sheath 902 in multiple longitudinal regions thereof.

While various embodiments have been described above, it should be understood that they have been presented only as illustrations and examples of the present invention, and not by way of limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A steerable catheter comprising:
   a tubular sheath having a lumen formed within a wall thereof; and
   a steering mechanism disposed within the lumen, the steering mechanism comprising first and second steering components with at least a segment of the second steering component being coaxially disposed within the first steering component, wherein the first steering component and the second steering component are separately tensioned to bend respective regions of the tubular sheath.

2. The catheter of claim 1, wherein a distal end of the first steering component is attached at a first anchor point to the tubular sheath and a distal end of the second steering component is attached at a second anchor point to the tubular sheath and wherein the second anchor point is distal of the first anchor point.

3. The catheter of claim 2, wherein the first anchor point is proximally spaced from a distal end of the tubular sheath such that tensioning of the first steering component bends a proximal region of the catheter to a first radius of curvature.

4. The catheter of claim 3, wherein the second anchor point is at the distal end of the tubular sheath such that tensioning of the second steering component bends a distal region of the catheter to a second radius of curvature.

5. The catheter of claim 4, wherein the first and second radii of curvature are different from each other.

6. The catheter of claim 2, wherein a distal segment of the second steering component extends from the distal end of the first steering component to the second anchor point and is slidably disposed within a corresponding distal portion of the lumen of the tubular sheath.

7. A steerable guide catheter comprising:
a tubular sheath defining a central lumen sized to receive a medical device there-through, wherein a longitudinally-extending lumen is formed with a wall of the tubular sheath;
a pull tube defining a pull wire lumen, the pull tube having a distal end attached at a first anchor point to the tubular sheath and having at least a segment slidably disposed within the longitudinally-extending lumen of the tubular sheath; and
a pull wire having a distal end attached at a second anchor point to the tubular sheath and having at least a segment slidably disposed within the pull wire lumen of the pull tube, wherein the second anchor point is distal of the first anchor point, and
wherein the pull tube and the pull wire are separately tensioned to bend respective regions of the tubular sheath.

8. The guide catheter of claim 7, wherein the first anchor point is proximally spaced from a distal end of the tubular sheath such that tensioning of the pull tube bends a proximal region of the guide catheter to a first radius of curvature.

9. The guide catheter of claim 8, wherein the second anchor point is at the distal end of the tubular sheath such that tensioning of the pull wire bends a distal region of the guide catheter to a second radius of curvature.

10. The guide catheter of claim 9, wherein the first and second radii of curvature are different from each other.

11. The guide catheter of claim 9, wherein the proximal region is proximal of the distal end of the pull tube and the distal region is distal of the distal end of the pull tube.

12. The guide catheter of claim 7, wherein the segments of the pull tube and the pull wire are coaxially disposed within the longitudinally-extending lumen of the tubular sheath.

13. The guide catheter of claim 7, wherein a distal segment of the pull wire extends from the distal end of the pull tube to the second anchor point and is slidably disposed within a corresponding distal portion of the longitudinally-extending lumen of the tubular sheath.

14. A steerable delivery system for a prosthesis comprising:
a tubular sheath defining a central lumen and having a lumen formed within a wall thereof;
a pull tube having at least a segment slidably disposed in the lumen within the wall of the tubular sheath;
a pull wire having at least a segment slidably disposed within the pull tube, wherein a distal end of the pull tube is attached at a first anchor point to the tubular sheath and a distal end of the pull wire is attached at a second anchor point to the tubular sheath and wherein the second anchor point is distal of the first anchor point; and
wherein the pull tube and the pull wire are separately tensioned to bend respective regions of the tubular sheath.

15. The delivery system of claim 14, wherein a distal portion of the tubular sheath is configured to hold the prosthesis in a compressed, delivery configuration and wherein a distal end of the distal portion is the distal end of the tubular sheath.

16. The delivery system of claim 15, wherein the first anchor point is at a proximal end of the distal portion and the second anchor point is at the distal end of the distal portion.

17. The delivery system of claim 16, wherein tensioning of the pull tube bends a proximal portion of the tubular sheath to a first radius of curvature.

18. The delivery system of claim 17, wherein tensioning of the pull wire bends the distal portion of the tubular sheath to a second radius of curvature.

19. The delivery system of claim 18, wherein the first and second radii of curvature are different from each other.

20. The delivery system of claim 14, wherein a distal segment of the pull wire extends from the distal end of the pull tube to the second anchor point and is slidably disposed within a corresponding distal portion of the lumen formed within the wall of the tubular sheath.

* * * * *